(12) United States Patent
Kwon et al.

(10) Patent No.: US 12,258,322 B2
(45) Date of Patent: Mar. 25, 2025

(54) METHODS FOR PREPARING DIHYDROXYAMMONIUM 5,5'-BISTETRAZOLE-1,1'DIOLATE

(71) Applicant: AGENCY FOR DEFENSE DEVELOPMENT, Daejon (KR)

(72) Inventors: Kuk Tae Kwon, Daejon (KR); Hae Wook Yoo, Daejon (KR); Seung Hee Kim, Daejon (KR); So Jung Lee, Daejon (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 18/706,706

(22) PCT Filed: Jun. 1, 2023

(86) PCT No.: PCT/KR2023/007481
§ 371 (c)(1),
(2) Date: May 1, 2024

(87) PCT Pub. No.: WO2023/239104
PCT Pub. Date: Dec. 14, 2023

(65) Prior Publication Data
US 2024/0425466 A1 Dec. 26, 2024

(30) Foreign Application Priority Data

Jun. 7, 2022 (KR) .................. 10-2022-0068969

(51) Int. Cl.
C07D 257/04 (2006.01)
C07C 249/08 (2006.01)
C07C 249/12 (2006.01)
C07D 309/12 (2006.01)

(52) U.S. Cl.
CPC .......... C07D 257/04 (2013.01); C07C 249/08 (2013.01); C07C 249/12 (2013.01); C07D 309/12 (2013.01)

(58) Field of Classification Search
CPC .................................................. C07D 257/04
See application file for complete search history.

(56) References Cited

FOREIGN PATENT DOCUMENTS

| CN | 103524444 A | 1/2014 |
| CN | 104829548 A | 8/2015 |
| KR | 101964988 B1 | 4/2019 |
| KR | 102102357 B1 | 4/2020 |
| KR | 102128565 B1 | 6/2020 |

*Primary Examiner* — David K O'Dell
(74) *Attorney, Agent, or Firm* — Hodgson Russ LLP

(57) ABSTRACT

The present invention relates to a method for preparing dihydroxyammonium 5,5'-bistetrazole-1,1'-diolate. The method for preparing dihydroxyammonium 5,5'-bistetrazole-1,1'-diolate, according to one embodiment of the present invention, comprises the steps of: synthesizing 5,5'-bistetrazole-1,1'-diol dihydrate (1,1'-BTO) from ditetrahydropyranyl diazidoglyoxime (THP-DAG) by using a hydrochloric acid (HCl) solution in a first solvent; and reacting 1,1'-BTO with an amine solution so as to neutralize same and, simultaneously, obtaining dihydroxylammonium 5,5'-bistetrazole-1,1'-diolate (Thomas Klapotke explosive-50, TKX-50).

11 Claims, 2 Drawing Sheets

METHODS FOR PREPARING DIHYDROXYAMMONIUM 5,5'-BISTETRAZOLE-1,1'DIOLATE

TECHNICAL FIELD

The present disclosure relates to a method of preparing dihydroxylammonium 5,5'-bistetrazole-1,1'-diolate.

BACKGROUND ART

High-performance molecular explosives currently widely used in warheads are 1,3,5-trinitro-1,3,5-triazacyclohexane (RDX) and 1,3,5,7-tetranitro-1,3,5,7-tetraazacyclooctane (HMX), and these explosives were developed in the 1900s and have been used for a long time. Many studies are being actively conducted around the world to develop explosives with better performance than RDX or HMX. However, since in general, as performance increases, sensitivity tends to increase, handling and operation are limited for safety reasons.

The ultimate goal of development of molecular explosives is to increase performance and reduce sensitivity. As part of such research, active research has recently been conducted on azole-based compounds that are aromatic ring compounds containing nitrogen.

Dihydroxylammonium 5,5'-bistetrazole-1,1'-diolate (Thomas Klapotke explosive-50 (TKX-50)), which is a tetrazole compound published in 2012, is one of compounds that is attracting the most attention as a molecular explosive to replace HMX. Characteristics of several molecular explosives, including TKX-50, are shown in Table 1.

TABLE 1

|  | RDX | HMX | CL-20 | TKX-50 |
|---|---|---|---|---|
| Decomposition temperature [° C.] | 210 | 279 | 215 | 221 |
| Density [g/cm$^3$] | 1.806 | 1.904 | 2.035 | 1.877 |
| Impact sensitivity [J] | 7.5 | 7 | 4 | 20 |
| Friction sensitivity [N] | 120 | 112 | 48 | 120 |
| Detonation pressure [kbar] | 380 | 415 | 467 | 424 |
| Detonation velocity [m/s] | 8983 | 9221 | 9455 | 9698 |

TKX-50 is synthesized through five steps using glyoxal as a starting material. FIG. 1 is a diagram illustrating a method of preparing dihydroxylammonium 5,5'-bistetrazole-1,1'-diolate (TKX-50) according to a related art. Referring to FIG. 1, such a synthesis method has issues in that diazidoglyoxime (DAG), which is an intermediate, is extremely sensitive, and in that highly corrosive hydrochloric acid gas is used in a step of synthesizing tetrazole.

Table 2 shows a comparison of sensitivity characteristics of diazidoglyoxime, which is an intermediate, and two primary explosives. The sensitivity of diazidoglyoxime, which is an intermediate, obtained after an azide group that is an energy group is introduced is similar to those of the primary explosives, which indicates that the diazidoglyoxime exhibits extremely sensitive characteristics.

TABLE 2

|  | Lead Styphnate | Lead azide | Diazidoglyoxime |
|---|---|---|---|
| Impact sensitivity [J] | 2.5-5 | 2.5-4 | 1.5 |
| Friction sensitivity [N] | 1.5 | 0.1-1 | 5 or less |

To solve an issue of sensitivity of an intermediate, research results on desensitization of intermediates by introducing protecting groups have been published. Although research results have been reported on the use of a hydrochloric acid solution to replace the use of hydrochloric acid gas, there is still a limitation of mass production due to a generation of corrosive gas in a process in which the hydrochloric acid solution itself needs to be refluxed at a high temperature or removed under reduced pressure.

In addition, since the above research results are applied to a liquid-liquid extraction process, scale-up is limited.

DISCLOSURE OF THE INVENTION

Technical Goals

To solve the above-described problems, an aspect of the present disclosure is to provide a method of preparing dihydroxylammonium 5,5'-bistetrazole-1, l'-diolate that may replace a liquid-liquid extraction process with a precipitation process, may exclude use of hydrochloric acid gas, and may perform a next reaction through a neutralization in one container instead of removing a hydrochloric acid solution using air or decompression even when the hydrochloric acid solution is used, to suppress a generation of corrosive gas and facilitate scale-up.

However, goals to be achieved are not limited to those described above, and other goals not mentioned above can be clearly understood by one of ordinary skill in the art from the following description.

Technical Solutions

A method of preparing dihydroxylammonium 5,5'-bistetrazole-1,l'-diolate (Thomas Klapotke explosive-50, TKX-50) according to an embodiment of the present disclosure includes steps of synthesizing 5,5'-bistetrazole-1,l'-diol dihydrate (1,1'-BTO) from ditetrahydropyranyl diazidoglyoxime (THP-DAG) using a hydrochloric acid (HCl) solution in a first solvent: and obtaining dihydroxylammonium 5,5'-bistetrazole-1, l'-diolate (Thomas Klapotke explosive-50, TKX-50), and simultaneously, reacting and neutralizing the 1, l'-BTO and an amine solution.

In an embodiment, the step of synthesizing the 1,1'-BTO may include adding the THP-DAG and the first solvent to a reactor, adding an HCl solution with a concentration of 20% to 50%, and performing stirring in a temperature range of 30° C. to 60° C.

In an embodiment, the step of obtaining the TKX-50 may include forming a solution by adding sodium hydroxide (NaOH) after dissolving an amine solution and an HCl solution in water: preparing an amine-containing solution by adding water: adding the 1, l'-BTO and the amine-containing solution to the first solvent: performing stirring for 10 minutes to 40 minutes while maintaining a temperature range of 30° C. to 50° C.: raising a temperature of a reactor to a temperature of 70° C. to 90° C. and performing stirring for 20 minutes to 60 minutes: adding an amine solution: performing stirring: performing cooling by lowering a reaction temperature of a solution to a temperature of 1° C. to 10° C.: and performing a filtration, to precipitate TKX-50).

In an embodiment, the first solvent may include at least one selected from a group consisting of tetrahydrofuran (THF), dimethylformamide (DMF), dimethylacetamide (DMAc), N-methyl-2-pyrrolidone (NMP), and m-cresol.

In an embodiment, the amine-containing solution may include at least one selected from a group consisting of hydroxylamine ($NH_2OH$), ethanolamine, N-aminoethylethanolamine, diethanolamine. 2-hydroxypropylamine, N,N-bis-(2-hydroxypropyl) amine (diisopropanolamine), N,N'-bis-(2-hydroxyethyl) ethylene diamine, and neopentanolamine.

In an embodiment, the method may further include, prior to the step of synthesizing the 1,1'-BTO, steps of synthesizing glyoxime by reacting glyoxal and hydroxylamine: synthesizing dichloroglyoxime (DCG) from the glyoxime: synthesizing ditetrahydropyranyl dichloroglyoxime (THP-DCG) from the DCG: and synthesizing ditetrahydropyranyl diazidoglyoxime (THP-DAG) from the THP-DCG.

In an embodiment, the step of synthesizing the glyoxime may include reacting the glyoxal and the amine solution with sodium hydroxide (NaOH) in an aqueous solution, and the amine solution may include at least one selected from a group consisting of hydroxylamine ($NH_2OH$), ethanolamine, N-aminoethylethanolamine, diethanolamine, 2-hydroxypropylamine, N,N-bis-(2-hydroxypropyl) amine (diisopropanolamine), N,N'-bis-(2-hydroxyethyl) ethylene diamine, and neopentanolamine.

In an embodiment, the step of synthesizing the DCG may include reacting the glyoxime with a halogenating agent under a second solvent, and the second solvent may include at least one organic solvent selected from a group consisting of N,N'-dimethylformamide (DMF), dimethylacetamide, N-methyl-2-pyrrolidone, tetrahydrofuran, diethyl ether, dichloromethane, chloroform, and toluene.

In an embodiment, the halogenating agent may include at least one selected from a group consisting of N-chlorosuccinimide, N-bromosuccinimide, and N-iodosuccinimide.

In an embodiment, the step of synthesizing the THP-DCG may be performed by using p-toluenesulfonic acid (p-TsOH) as a catalyst under a third solvent and reacting the DCG with 3,4-dihydro-2H-pyran, and the third solvent may include at least one halogenated organic solvent selected from a group consisting of dichloromethane (DCM), chloroform, and dichloroethane.

In an embodiment, after a reaction of the DCG, the p-TsOH, and the 3,4-dihydro-2H-pyran, the first solvent and water may be added and reacted at a temperature of 50° C. to 80° C. for 1 hour to 3 hours. A reaction temperature may be lowered to room temperature, acetone may be added, and cooling may be performed by lowering a temperature to a temperature of 1° C. to 10° C. to precipitate a solid, and a filtration and washing may be performed, to precipitate THP-DCG.

In an embodiment, the step of synthesizing the THP-DAG may include reacting the

THP-DCG with an azide salt under N,N'-dimethylformamide (DMF).

In an embodiment, the THP-DCG, the DMF, and the azide salt may be stirred at a temperature of 90° C. to 120° C. for 1 hour to 3 hours and then cooled to a temperature of 60° C. to 80° C. Distilled water may be added, and cooling may be performed by lowering a temperature to a temperature of 1° C. to 10° C. to precipitate a solid, to precipitate THP-DAG.

In an embodiment, the azide salt may include at least one selected from a group consisting of sodium azide ($NaN_3$), potassium azide ($KN_3$), and lithium azide ($LiN_3$).

Effect of the Invention

According to an embodiment of the present disclosure, a method of preparing dihydroxylammonium 5,5'-bistetrazole-1,1'-diolate, which may replace a liquid-liquid extraction process with a precipitation process, may exclude use of hydrochloric acid gas, and may perform a next reaction through a neutralization in one container instead of removing a hydrochloric acid solution using air or decompression even when the hydrochloric acid solution is used, may be effective in suppressing a generation of corrosive gas and facilitating scale-up.

BEST MODE FOR CARRYING OUT THE INVENTION

Figure 1:
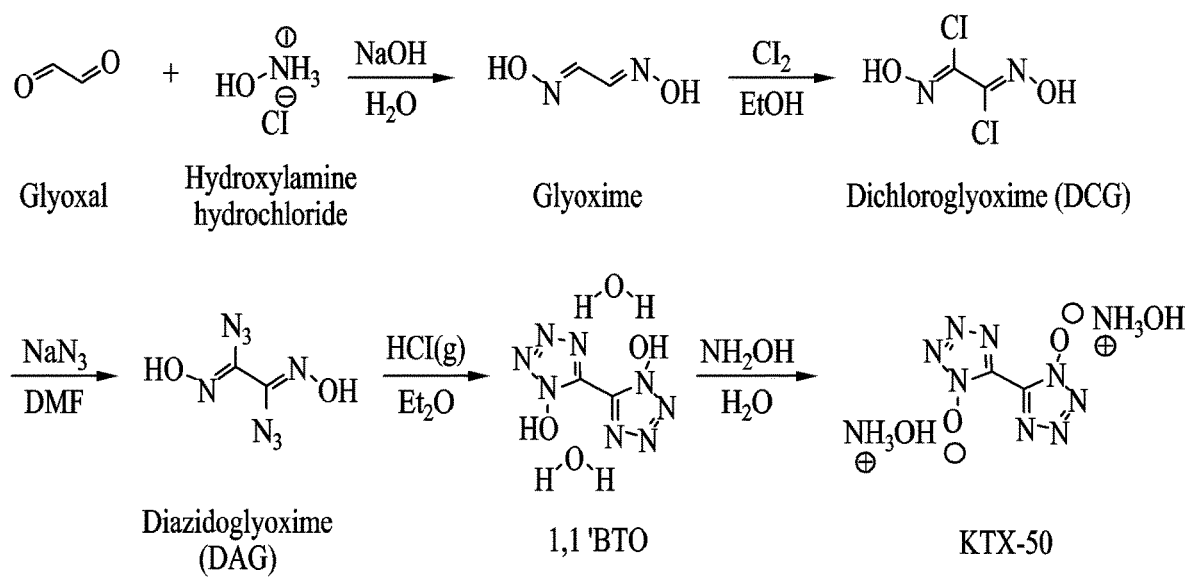
FIG. 1 is a diagram illustrating a method of preparing dihydroxylammonium 5,5'-bistetrazole-1,1'-diolate (TKX-50) according to a related art.

Hereinafter, embodiments will be described in detail with reference to the accompanying drawings. However, various alterations and modifications may be made to the embodiments. Here, the embodiments are not meant to be limited by the descriptions of the present disclosure. The embodiments should be understood to include all changes, equivalents. and replacements within the idea and the technical scope of the disclosure. The terminology used herein is for the purpose of describing particular embodiments only and is not intended to be limiting. The singular forms "a," "an," and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps. operations, elements, components and/or groups thereof.

Unless otherwise defined, all terms including technical and scientific terms used herein have the same meaning as commonly understood by one of ordinary skill in the art to which the embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

In addition, when describing the embodiments with reference to the accompanying drawings, like reference numerals refer to like components and a repeated description related thereto will be omitted. In the description of embodiments, detailed description of well-known related structures or functions will be omitted when it is deemed that such description will cause ambiguous interpretation of the present disclosure.

In addition, the terms first, second, A, B, (a), and (b) may be used to describe components of the embodiments. These terms are used only for the purpose of discriminating one component from another component, and the nature, the sequences, or the orders of the components are not limited by the terms.

Components included in one embodiment and components having a common function will be described using the same names in other embodiments. Unless otherwise mentioned, the descriptions on the embodiments may be applicable to the following embodiments and thus, duplicated descriptions will be omitted for conciseness.

Hereinafter, a method of preparing dihydroxylammonium 5,5'-bistetrazole-1,1'-diolate according to the present disclosure will be described in detail with reference to embodiments and drawings. However, the present disclosure is not limited to the embodiments and drawings. A method of preparing dihydroxylammonium 5,5'-bistetrazole-1,1'-diolate (Thomas Klapotke explosive—50 (TKX-50) according to an embodiment of the present disclosure includes steps of: synthesizing 5,5'-bistetrazole-1,1'-diol dihydrate (1,1'-BTO) from ditetrahydropyranyl diazidoglyoxime (THP-DAG) using a hydrochloric acid (HCl) solution in a first solvent: and obtaining dihydroxylammonium 5,5'-bistetrazole-1,1'-diolate (Thomas Klapotke explosive-50, TKX-50), and simultaneously, reacting and neutralizing the 1,1'-BTO and an amine solution.

Figure 2:
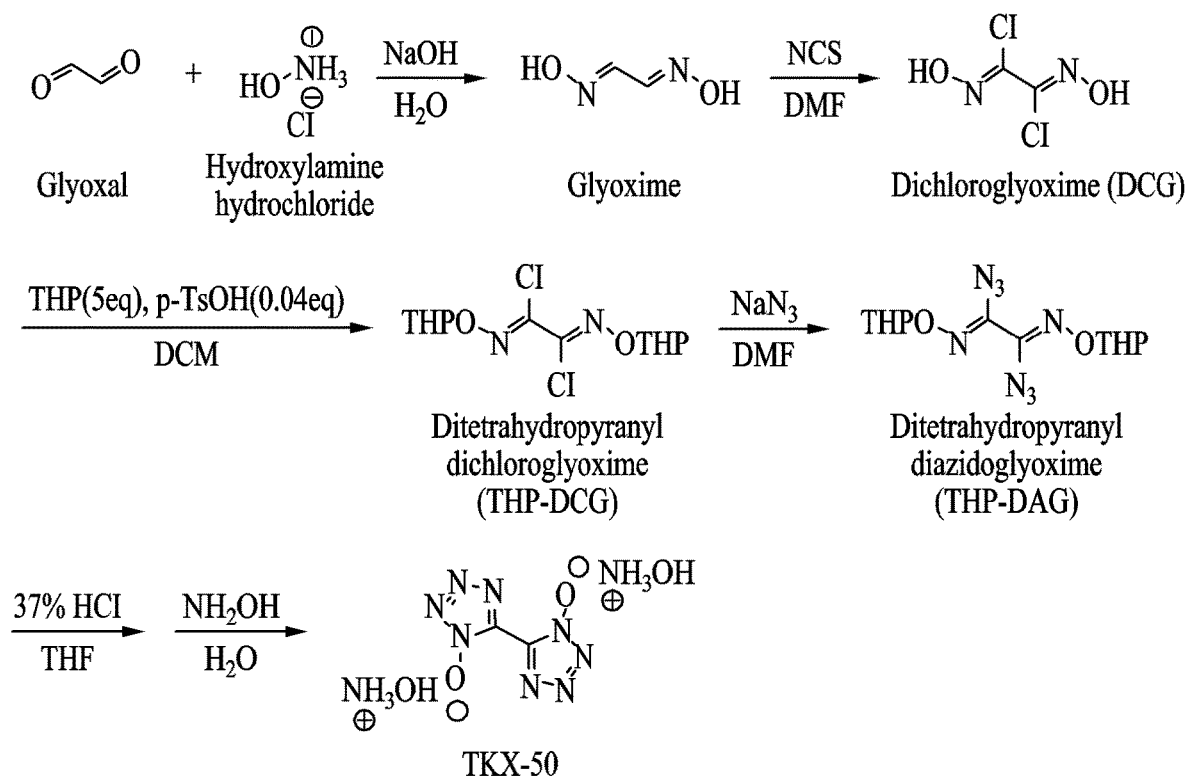
FIG. 2 is a diagram illustrating a method of preparing dihydroxylammonium 5,5'-bistetrazole-1,1'-diolate (TKX-50)) according to an embodiment of the present disclosure.

FIG. 2 is a diagram illustrating a method of preparing dihydroxylammonium 5,5'-bistetrazole-1,1'-diolate (TKX-50)) according to an embodiment of the present disclosure.

The method of preparing the TKX-50 according to an embodiment of the present disclosure may include a step of synthesizing 1,1'-BTO and a step of obtaining TKX-50.

In an embodiment, the step of synthesizing 1,1'-BTO may include adding the THP-DAG and the first solvent to a reactor, adding an HCl solution with a concentration of 20% to 50%, performing stirring in a temperature range of 30° C. to 60° C., dissolving an amine solution and the HCl solution in water, adding sodium hydroxide (NaOH) to form a solution, and water may be added, to prepare an amine-containing solution.

In an embodiment, the first solvent may include at least one selected from a group consisting of tetrahydrofuran (THF), dimethylformamide (DMF), dimethylacetamide (DMAc), N-methyl-2-pyrrolidone (NMP), and m-cresol.

Desirably, the first solvent may be tetrahydrofuran (THF).

In an embodiment, the HCl solution may have a concentration of 20% to 50%: 20% to 40%: 20% to 30%: 30% to 50%: 30% to 40%; and 40% to 50%.

Desirably, the HCl solution may have a concentration of 30% to 40%. For example, the step of synthesizing the 1,1'-BTO may include adding THP-DAG and tetrahydrofuran (THF) to the reactor, adding the HCl solution, raising a temperature of a solution to a temperature of 30° C. to 50° C., and performing stirring for 2 to 5 hours.

In an embodiment, the step of obtaining the TKX-50 may include forming a solution by adding sodium hydroxide (NaOH) after dissolving an amine solution and an HCl solution in water: preparing an amine solution by adding water: adding the 1, l'-BTO and the amine-containing solution to the first solvent: performing stirring for 10 minutes to 40 minutes while maintaining a temperature range of 30° C. to 50° C.: raising a temperature of a reactor to a temperature of 70° C. to 90° C. and performing stirring for 20 minutes to 60 minutes: adding an amine solution: performing stirring: performing cooling by lowering a reaction temperature of a solution to a temperature of 1° C. to 10° C.: and performing a filtration, to precipitate TKX-50.

In an embodiment, the first solvent may include at least one selected from a group consisting of tetrahydrofuran (THF), dimethylformamide (DMF), dimethylacetamide (DMAc), N-methyl-2-pyrrolidone (NMP), and m-cresol.

In an embodiment, the amine solution may include at least one selected from a group consisting of hydroxylamine (NH₂OH), ethanolamine, N-aminoethylethanolamine, diethanolamine, 2-hydroxy propylamine, N,N-bis-(2-hydroxypropyl) amine (diisopropanolamine), N,N'-bis-(2-hydroxyethyl) ethylene diamine, and neopentanolamine.

Desirably, the amine solution may be hydroxylamine (NH₂OH).

For example, a step of synthesizing the TKX-50 may include forming a solution by dissolving NH₂OH· HCl in water and adding NaOH, and adding water, to prepare a transparent NH₂OH solution. The 1, l'-BTO and the prepared NH₂OH solution may be added to the reacted THF solution, and stirring may be performed for 10 minutes to 60 minutes while maintaining a temperature of 30° C. to 50° C. The temperature of the reactor may be raised to a temperature of 70° C. to 90° C., and stirring may be performed for 20 minutes to 50 minutes. The prepared NH₂OH solution may be slowly added to the above solution, and stirring may be performed for 30 minutes to 2 hours. A temperature of the solution may be slowly lowered to 5° C., and a filtration may be performed, to obtain TKX-50.

The method of preparing the TKX-50 of the present disclosure may be synthesizing TKX-50, and simultaneously, reacting and neutralizing 1, l'-BTO and an excess amine solution in one-pot instead of removing a corrosive acidic solvent.

In an embodiment, the method may further include, prior to the step of synthesizing the 1,l'-BTO, a step of synthesizing glyoxime by reacting glyoxal and hydroxylamine: a step of synthesizing dichloroglyoxime (DCG) from the glyoxime: a step of synthesizing ditetrahydropyranyl dichloroglyoxime (THP-DCG) from the DCG: and a step of synthesizing ditetrahydropyranyl diazidoglyoxime (THP-DAG) from the THP-DCG.

In an embodiment, the step of synthesizing the glyoxime may include reacting the glyoxal and the amine solution with sodium hydroxide (NaOH) in an aqueous solution.

In an embodiment, the amine solution may include at least one selected from a group consisting of hydroxylamine (NH₂OH), ethanolamine, N-aminoethylethanolamine, diethanolamine, 2-hydroxy propylamine, N,N-bis-(2-hydroxypropyl)amine(diisopropanolamine), N,N'-bis-(2-hydroxyethyl) ethylene diamine, and neopentanolamine.

Desirably, the amine solution may be hydroxylamine (NH₂OH).

For example, the step of synthesizing the glyoxime may include adding sodium hydroxide (NaOH) and distilled water to the reactor, performing cooling to 0° C., and adding hydroxylamine hydrochloride to the reactor. Subsequently, an aqueous glyoxal solution with a concentration of 20% to 50% may be added to the reactor while maintaining a temperature of 0° C. to 10° C. Stirring may be performed for 30 minutes to 2 hours while maintaining the internal temperature of the reactor at 0° C., and if a solid is formed, a filtration may be performed, and washing with a small amount of ice water may be performed. Subsequently, drying may be performed, to obtain glyoxime.

In an embodiment, the step of synthesizing the DCG may include reacting the glyoxime with a halogenating agent under a second solvent.

The synthesized DCG may be in the form of one molecule of DCG bound to one molecule of the second solvent.

In an embodiment, the second solvent may include at least one organic solvent selected from a group consisting of N,N'-dimethylformamide (DMF), dimethylacetamide, N-methyl-2-pyrrolidone, tetrahydrofuran, diethyl ether, dichloromethane, chloroform, and toluene.

Desirably, the second solvent may be N,N'-dimethylformamide (DMF).

In an embodiment, the halogenating agent may include at least one selected from a group consisting of N-chlorosuccinimide, N-bromosuccinimide, and N-iodosuccinimide.

Desirably, the halogenating agent may be N-chlorosuccinimide.

For example, the step of synthesizing the DCG may include adding DMF to the reactor, performing heating at a temperature of 40° C. to 60° C., and slowing adding N-chlorosuccinimide such that the internal temperature of the reactor does not exceed 60° C. Stirring may be performed for 1 hour to 2 hours while maintaining the internal temperature of the reactor at 50° C. Subsequently, distilled water may be added, and an obtained solid may be filtered/dried, to obtain DCGDMF in which one molecule of DMF is bound to one molecule of dichloroxime.

In an embodiment, the step of synthesizing the THP-DCG may be performed by using p-toluenesulfonic acid (p-TsOH) as a catalyst under a third solvent and reacting the DCG with 3,4-dihydro-2H-pyran.

3,4-dihydro-2H-pyran may be an inactive group.

In an embodiment, the third solvent may include at least one halogenated organic solvent selected from a group consisting of dichloromethane (DCM), chloroform, and dichloroethane.

Desirably, the third solvent may be dichloromethane (DCM).

In an embodiment, after a reaction of the DCG, the p-TsOH, and the 3,4-dihydro-2H-pyran, the first solvent and water may be added and reacted at a temperature of 50° C. to 80° C. for 1 hour to 3 hours. A reaction temperature may be lowered to room temperature, acetone may be added, and cooling may be performed by lowering a temperature to a temperature of 1° C. to 10° C. to precipitate a solid, and a filtration and washing may be performed, to precipitate THP-DCG.

In an embodiment, the first solvent may include at least one selected from a group consisting of tetrahydrofuran (THF), dimethylformamide (DMF), dimethylacetamide (DMAc), N-methyl-2-pyrrolidone (NMP), and m-cresol.

Desirably, the first solvent may be tetrahydrofuran (THF).

For example, the step of synthesizing the THP-DCG may include using p-TsOH as a catalyst under DCM, setting the temperature of the reactor to a temperature of 15° C. to 25° C., slowly adding the DCG and 3,4-dihydro-2H-pyran such that the temperature does not exceed a temperature of 20° C. to 40° C., and performing stirring at a temperature of 20° C. to 40° C. for 20 minutes to 60) minutes. In addition, the same amount of 3,4-dihydro-2H-pyran may be additionally added, and stirring may be additionally performed at a temperature of 20° C. to 40° C. for 1 hour to 3 hours. Subsequently, THF and water may be added, a temperature of a jacket may be raised to a temperature of 50° C. to 70° C., stirring may be performed for 1 hour to 3 hours, the reaction temperature may be lowered to room temperature, alcohol may be added, and the temperature may be lowered to a temperature of 1° C. to 10° C. to precipitate a solid, and a filtration, washing, and drying may be performed, to precipitate the THP-DCG.

In an embodiment, the step of synthesizing the THP-DAG may include reacting the THP-DCG with an azide salt under N,N'-dimethylformamide (DMF). Here, an azidation may be performed by reacting the THP-DCG with the azide salt, to synthesize the THP-DAG.

In an embodiment, the azide salt may include at least one selected from a group consisting of sodium azide ($NaN_3$), potassium azide ($KN_3$), and lithium azide ($LiN_3$).

Desirably, the azide salt may be sodium azide ($NaN_3$).

In an embodiment, the THP-DCG, the DMF, and the azide salt may be stirred at a temperature of 90° C. to 120° C. for 1 hour to 3 hours and cooled to a temperature of 60° C. to 80° C., distilled water may be added, cooling may be performed by lowering a temperature to a temperature of 1° C. to 10° C., and a solid may be precipitated, to precipitate the THP-DAG.

In the method of preparing the dihydroxylammonium 5,5'-bistetrazole-1, 1'-diolate (TKX-50)) according to an embodiment of the present disclosure, the HCl solution, instead of highly corrosive hydrochloric acid gas, may be used, and a process of refluxing the HCl solution or distilling the HCl solution under reduced pressure is not performed in the method, and thus, the method may be eco-friendly and enable mass production without generating corrosive gas. In addition, mass production may be facilitated by applying a solid precipitation process in the entire reaction process, instead of a liquid-liquid extraction process.

Hereinafter, the present disclosure will be described in more detail with reference to examples.

However, the following examples are given to illustrate the present disclosure, and the present disclosure is not limited to the examples.

Example 1: Synthesis of Glyoxime 18.4 g (0.46 mol) of NaOH and 50 mL of distilled water were added to a reactor, cooled to 0° C., and 46 g (0.66 mol) of hydroxylamine hydrochloride was added to the reactor. Subsequently, 47.9 g (0.33 mol) of a 40% aqueous glyoxal solution was added to the reactor while maintaining a temperature of 0) to 10° C. When a solid is produced after stirring for 1 hour while maintaining an internal temperature of the reactor at 0° C., a filtration and washing with a small amount of ice water were performed. Subsequently, drying was performed, to obtain 24.7 g (0.28 mol, 85%) of glyoxime.

$^1$H NMR (DMSO-$d_6$): 7.73 (s, 2H, CH), 11.61 (s, 2H, OH): $^{13}$C NMR (DMSO-$d_6$): 145.82

Example 2: Synthesis of Dichloroglyoxime (DCG)

10 g (0.113 mol) of glyoxime and 40 mL of DMF were added to the reactor, heated to 50° C., and 30.8 g (0.231 mol) of N-chlorosuccinimide was slowly added to the reactor. Here, the internal temperature of the reactor was prevented from exceeding 60° C. Stirring was performed for 1 hour and 30 minutes while maintaining the internal temperature of the reactor at 50° C. Subsequently, after 40 mL of distilled water was added, the obtained solid was filtered/dried, to obtain 19.8 g (0.086 mol, 76%) of DCG·DMF in which one molecule of dichloroglyoxime and one molecule of N,N'-dimethylformamide were bound.

$^1$H NMR (DMSO-$d_6$): 13.15 (s, 2H, OH), 7.94 (s, 1H, CH), 2.88 (s, 3H, $CH_3$), 2.73 (s, 3H, $CH_3$): $^{13}$C NMR (DMSO-$d_6$): 162.85, 131.20, 36.31, 31.30

Example 3: Synthesis of Ditetrahydropyranyl dichloroglyoxime (THP-DCG)

40.00 g (173.9 mmol) of DCG· DMF, 160 mL of DCM, and 0.64 g (3.36 mmol) of p-Toluenesulfonic acid (p-TsOH) were added to the reactor, and the temperature of the reaction was set to 20° C. 20 mL (257.9 mmol) of 3,4-dihydro-2H-pyran was slowly added such that the temperature did not exceed 30° C., and then stirred at 30° C. for 30 minutes. 0.64 g (3.36 mmol) of p-TsOH and 20 mL (257.9 mmol) of 3,4-dihydro-2H-pyran were additionally added and additionally stirred at 30° C. for 2 hours. 40 mL of tetrahydrofuran (THF) and 40 ml of water were added, a temperature of a jacket was raised to 60° C., and stirring was performed for 1 hour and 30 minutes. The reaction temperature was lowered to room temperature, 80 mL of acetone was added, and cooling was performed by lowering the temperature to 5° C. The precipitated solid was collected by filtration, washed with water, and dried, to obtain 31.8 g (97.8 mmol, 56%) of THP-DCG.

$^1$H NMR (CDCl$_3$): 1.64 (m, 8H, CH$_2$), 1.86 (m, 4H, CH$_2$), 3.75 (m, 4H, CH$_2$), 5.52 (m, 2H, CH); $^{13}$C NMR (CDCl$_3$): 18.80, 18.83, 25.16, 28.45, 28.47, 62.54, 62.62, 102.30, 102.36, 133.91, 133.96

Example 4: Synthesis of Ditetrahydropyranyl diazidoglyoxime (THP-DAG)

10 g (30.75 mmol) of THP-DCG, 100 mL of DMF, and 4.80 g (73.83 mmol) of NaN$_3$ were added to the reactor. The jacket temperature of the reactor was raised to 100° C., stirring was performed for 1 hour and 30 minutes, and cooling to 70° C. was performed. Subsequently, 100 mL of distilled water was slowly added and cooled, and THP-DAG was precipitated and filtered, to 8.4 g (24.82 mmol, 80.7%) of THP-DAG.

$^1$H NMR (CDCl$_3$): 1.63 (m, 8H, CH$_2$), 1.80 (m, 4H, CH$_2$), 3.75 (m, 4H, CH$_2$), 5.34 (m, 2H, CH): $^{13}$C NMR (CDCl$_3$): 18.37, 18.45, 24.79, 28.01, 28.06, 62.10, 62.26, 101.72, 101.81, 137.80, 137.82: Impact sensitivity: 19.95 J, Friction sensitivity: 352.8 N, Electrostatic sensitivity: 50 mJ Example 5 Synthesis of Dihydroxylammonium 5,5'-bistetrazole-1,1'-diolate (TKX-50)

5.0 g (14.8 mmol) of THP-DAG and 25 mL of tetrahydrofuran (THF) were added to the reactor, and 1.25 mL (15.2 mmol) of a 37% HCl solution was added. A temperature of a solution was raised to 45° C., and stirring was performed for 4 hours.

A solution was formed by dissolving 7.0 g (100.7 mmol) of NH$_{20}$H. HCl in 15 mL of water and adding 3.0 g (75 mmol) of NaOH, and 4 mL of water was added, to prepare 25 mL (75 mmol) of a transparent NH$_2$OH solution.

7.5 mL (22.5 mmol) of the prepared NH$_2$OH solution was added to the THE solution reacted first, and stirring was performed for 30 minutes while maintaining the temperature at 45° C. The temperature of the reactor was raised to 85° C., and stirring was performed for 40 minutes. 17.5 mL (52.5 mmol) of the prepared NH$_2$OH solution was slowly added to the above solution, and stirring was performed for 1 hour.

The temperature of the solution was slowly lowered to 5° C., and a filtration was performed, to obtain 2.88 g (12.2 mmol, 82%) of dihydroxylammonium 5,5'-bistetrazole-1,1'-diolate (TKX-50).

$^1$H NMR (DMSO-d$_6$): 10.00 (s, 8H, NH$_3$OH): $^{13}$C NMR (DMSO-d$_6$): 135.45

An impact sensitivity, a friction sensitivity, and an electrostatic sensitivity of the obtained THP-DAG were measured using a BAM Fall Hammer, a BAM Friction Tester, and an Electrostatic Spark Sensitivity Tester.

The results obtained by measuring the sensitivity (the impact sensitivity, the friction sensitivity, and the electrostatic sensitivity) of the THP-DAG prepared according to Example 4 of the present disclosure show that the THP-DAG has an impact sensitivity of 19.95 J, a friction sensitivity of 352.8 N, and an electrostatic sensitivity of 50 mJ, which indicates that the THP-DAG is much more insensitive than the DAG.

In particular, the impact sensitivity/friction sensitivity of the THP-DAG are much lower than those of high-energy materials that are already in use, and work may be performed more safely than using existing synthesis methods from threats of explosion and fire accidents due to impact/friction/static electricity in handling of the THP-DAG. Table 3 shows sensitivity characteristics of DAG and THP-DAG.

TABLE 3

|  | Impact sensitivity [J] | Friction sensitivity [N] | Electrostatic sensitivity [mJ] |
| --- | --- | --- | --- |
| DAG | 1.5 | <5 | 7 |
| THP-DAG | 19.95 | 352.8 | 50 |

As described above, in the present disclosure, an effective synthesis method may be provided by replacing a liquid-liquid extraction process with a precipitation process during synthesizing of TKX-50, by performing a next reaction through a neutralization in one container instead of removing an HCl solution using air or decompression even when the HCl solution is used, to suppress a generation of corrosive gas and facilitate scale-up.

While the embodiments are described, it will be apparent to one of ordinary skill in the art that various alterations and modifications in form and details may be made in these embodiments without departing from the spirit and scope of the claims and their equivalents. For example, suitable results may be achieved if the described techniques are performed in a different order, and/or if components in a described system, architecture, device, or circuit are combined in a different manner, or replaced or supplemented by other components or their equivalents.

Therefore, other implementations, other embodiments, and equivalents to the claims are also within the scope of the following claims.

The invention claimed is:

1. A method of preparing dihydroxylammonium 5,5'-bistetrazole-1,1'-diolate, the method comprising steps of:
   synthesizing 5,5'-bistetrazole-1,1'-diol dihydrate (1,1'-BTO) from ditetrahydropyranyl diazidoglyoxime using a hydrochloric acid (HCl) solution in a first solvent; and
   obtaining dihydroxylammonium 5,5'-bistetrazole-1,l'-diolate, and simultaneously, reacting and neutralizing the 1,1'-BTO and an amine solution,
   wherein the step of synthesizing the 1, 1'-BTO comprises adding the ditetrahydropyranyl diazidoglyoxime and the first solvent to a reactor, adding an HCl solution with a concentration of 20% to 50%, and performing stirring in a temperature range of 30° C. to 60° C.,
   wherein the step of obtaining the dihydroxylammonium 5,5'-bistetrazole-1,1'-diolate comprises:
      forming a solution by dissolving an amine solution and an HCl solution in water and then adding sodium hydroxide (NaOH), and adding water, to prepare an amine-containing solution;
   adding the 1, 1'-BTO and the amine-containing solution to the first solvent;
   performing stirring for 10 minutes to 40 minutes while maintaining a temperature range of 30° C. to 50° C.; raising a temperature of a reactor to a temperature of 70° C. to 90° C. and performing stirring for 20 minutes to 60 minutes; adding an amine-containing solution;
   performing stirring; performing cooling by lowering a reaction temperature of a solution to a temperature of 1° C. to 10° C.; and performing a filtration, to precipitate dihydroxylammonium 5,5'-bistetrazole-1,1'-diolate, and wherein the first solvent comprises at least one selected from a group consisting of tetrahydrofuran (THF), dimethylformamide (DMF), dimethylacetamide (DMAc), N-methyl-2-pyrrolidone (NMP), and m-cresol.

2. The method of claim 1, wherein the amine solution comprises at least one selected from a group consisting of hydroxylamine ($NH_2OH$), ethanolamine, N-aminoethylethanolamine, diethanolamine, 2-hydroxypropylamine, N,N-bis-(2-hydroxypropyl) amine (diisopropanolamine), N,N'-bis-(2-hydroxyethyl) ethylene diamine, and neopentanolamine.

3. The method of claim 1, further comprising, prior to the step of synthesizing the 1,1'-BTO, steps of:
synthesizing glyoxime by reacting glyoxal and hydroxylamine;
synthesizing dichloroglyoxime (DCG) from the glyoxime;
synthesizing ditetrahydropyranyl dichloroglyoxime from the DCG; and
synthesizing ditetrahydropyranyl diazidoglyoxime from the ditetrahydropyranyl dichloroglyoxime.

4. The method of claim 3, wherein
the step of synthesizing the glyoxime comprises reacting the glyoxal and the amine solution with sodium hydroxide (NaOH) in an aqueous solution, and
the amine solution comprises at least one selected from a group consisting of hydroxylamine ($NH_2OH$), ethanolamine, N-aminoethylethanolamine, diethanolamine, 2-hydroxypropylamine, N,N-bis-(2-hydroxypropyl) amine (diisopropanolamine), N,N'-bis-(2-hydroxyethyl) ethylene diamine, and neopentanolamine.

5. The method of claim 3, wherein
the step of synthesizing the DCG comprises reacting the glyoxime with a halogenating agent under a second solvent, and
the second solvent comprises at least one organic solvent selected from a group consisting of N,N'-dimethylformamide (DMF), dimethylacetamide, N-methyl-2-pyrrolidone, tetrahydrofuran, diethyl ether, dichloromethane, chloroform, and toluene.

6. The method of claim 5, wherein the halogenating agent comprises at least one selected from a group consisting of N-chlorosuccinimide, N-bromosuccinimide, and N-iodosuccinimide.

7. The method of claim 3, wherein
the step of synthesizing the ditetrahydropyranyl dichloroglyoxime is performed by using p-toluenesulfonic acid (p-TsOH) as a catalyst under a third solvent and reacting the DCG with 3,4-dihydro-2H-pyran, and
the third solvent comprises at least one halogenated organic solvent selected from a group consisting of dichloromethane (DCM), chloroform, and dichloroethane.

8. The method of claim 7, wherein
after a reaction of the DCG, the p-TsOH, and the 3,4-dihydro-2H-pyran, the first solvent and water are added and reacted at a temperature of 50° C. to 80° C. for 1 hour to 3 hours, and
a reaction temperature is lowered to room temperature, acetone is added, and cooling is performed by lowering a temperature to a temperature of 1° C. to 10° C. to precipitate a solid, and a filtration and washing are performed, to precipitate ditetrahydropyranyl dichloroglyoxime.

9. The method of claim 3, wherein the step of synthesizing the ditetrahydropyranyl diazidoglyoxime comprises reacting the ditetrahydropyranyl dichloroglyoxime with an azide salt under N,N'-dimethylformamide (DMF).

10. The method of claim 9, wherein
the ditetrahydropyranyl dichloroglyoxime, the DMF, and the azide salt are stirred at a temperature of 90° C. to 120° C. for 1 hour to 3 hours and then cooled to a temperature of 60° C. to 80° C., and
distilled water is added, and cooling is performed by lowering a temperature to a temperature of 1° C. to 10° C. to precipitate a solid, to precipitate ditetrahydropyranyl diazidoglyoxime.

11. The method of claim 9, wherein the azide salt comprises at least one selected from a group consisting of sodium azide ($NaN_3$), potassium azide ($KN_3$), and lithium azide ($LiN_3$).

* * * * *